United States Patent

Tersteegen et al.

[11] 4,202,332
[45] May 13, 1980

[54] DOUBLE LUMEN CATHETER

[76] Inventors: Bernd Tersteegen; Günter Van Endert, both of Kreuzstrasse 19, D-4000 Düsseldorf 1, Fed. Rep. of Germany

[21] Appl. No.: 867,181

[22] Filed: Jan. 5, 1978

[30] Foreign Application Priority Data

Jan. 26, 1977 [DE] Fed. Rep. of Germany ....... 2703087

[51] Int. Cl.² .................... A61M 5/00; A61M 25/00
[52] U.S. Cl. ................... 128/214.4; 128/221; 128/349 R
[58] Field of Search .............. 128/214.4, 214.2, 221, 128/DIG. 16, 347, 340, 349 R

[56] References Cited

U.S. PATENT DOCUMENTS

| | | | |
|---|---|---|---|
| 3,082,769 | 3/1963 | Palmer | 128/221 |
| 3,388,703 | 6/1968 | Bowes | 128/214.4 |
| 3,492,992 | 2/1970 | Kurtz | 128/221 |
| 3,604,426 | 9/1971 | Erickson | 128/349 R |
| 3,610,239 | 10/1971 | Huggins | 128/214.4 |
| 3,612,050 | 10/1971 | Sheridan | 128/214.4 |
| 3,727,613 | 4/1973 | Sorenson et al. | 128/221 X |
| 3,863,632 | 2/1975 | Schwartz | 128/221 |
| 4,037,600 | 7/1977 | Poncy et al. | 128/214.4 |
| 4,054,139 | 10/1977 | Crossly | 128/348 X |
| 4,073,297 | 2/1978 | Kopp | 128/221 X |

FOREIGN PATENT DOCUMENTS

| | | | |
|---|---|---|---|
| 834211 | 10/1975 | Belgium | 128/214.4 |
| 7630263 | 10/1977 | Belgium | 128/214.4 |
| 1271898 | 7/1968 | Fed. Rep. of Germany | 128/214.4 |
| 1810804 | 11/1968 | Fed. Rep. of Germany | 128/214.4 |
| 1259977 | 5/1961 | France | 128/214.4 |
| 1530019 | 6/1968 | France | 128/214.4 |

Primary Examiner—E. H. Eickholt

[57] ABSTRACT

A double lumen catheter for use in haemodialysis, which comprises ducts for blood streams flowing into and respectively out of the body, an inner cannula providing an inner duct, an outer cannula surrounding the inner cannula and providing between the inner cannula and the outer cannula an outer duct, a front end of at least the inner cannula being inclined obliquely to the longitudinal cannula axis and sharply ground to facilitate puncture of a blood vessel, the front end of the inner cannula projecting beyond a front end of the outer cannula and the cross-section of the catheter changing progressively from the outer diameter of the inner cannula to the outer diameter of the outer cannula, the outer duct when in an operative state having at its front end an opening of cross-sectional area equal to the cross-sectional area of the outer duct, so that the total cross-section of the outer duct is available to a blood stream entering or leaving the outer duct.

9 Claims, 5 Drawing Figures

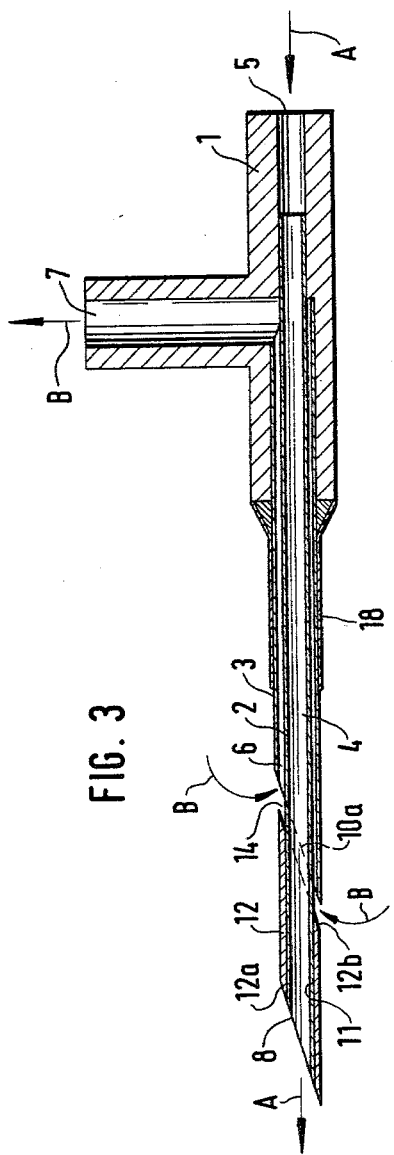

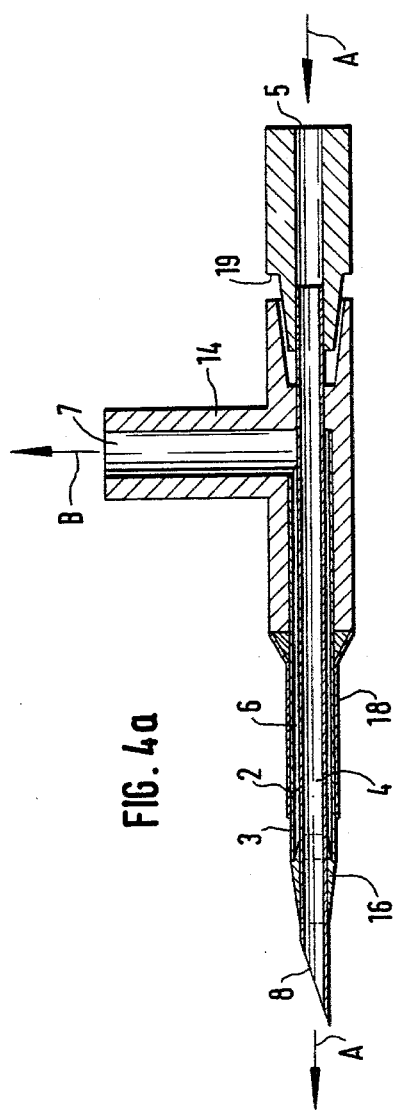
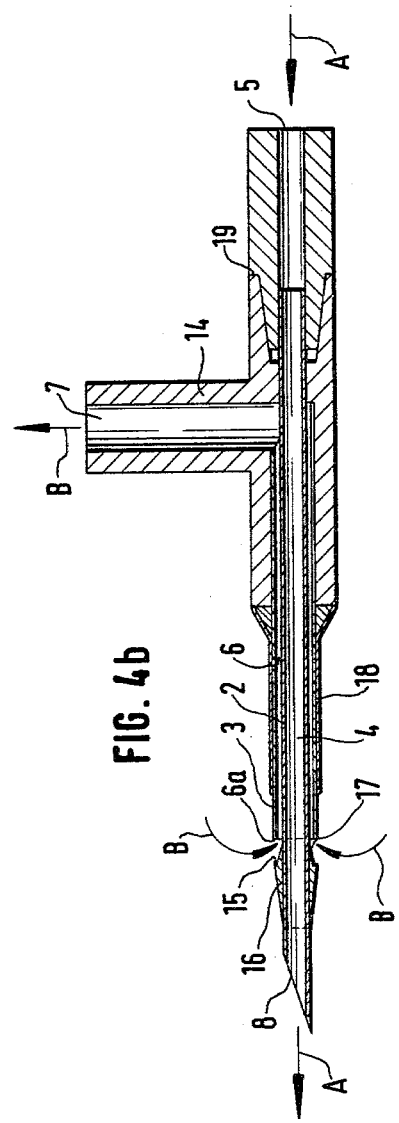
FIG. 4a
FIG. 4b

DOUBLE LUMEN CATHETER

This invention relates to a double lumen catheter, in particular for providing blood vessel access in extracorporeal haemodialysis, and having separate ducts for blood streams flowing into and out of the body.

Extra-corporeal haemodialysis is a process for treating chronic kidney failure in its final stage, which because of its life-saving effectiveness has gained general acceptance. In this process, the patient's blood is passed over a dialysing membrane for several hours during treatment at a rate of about 150 to 250 ml/min, and is thereafter immediately returned to the patient. Exchange of "urine poisons" from the blood takes place across the membrane into a dialysing solution flowing on the other side of the dialysing membrane. In order to maintain life, it is necessary for extra-corporeal haemodialysis to be carried out once or twice a week, each time for an average period of six hours. One problem of extra-corporeal haemodialysis is the problem of access to the blood vessel. For this, the so-called "Scribner Shunt" has become known. In this type of vessel access, there exists the drawback that new parts of the blood vessel must be continuously opened up, since the operational life of this type of blood vessel connection is limited due to typical complications such as formation of coagula or infection.

In providing access to a blood vessel, it has further become known to directly join together an artery and a vein generally in the lower arm, by sewing together an artery and vein in an operation. Because of the considerably higher blood pressure in the artery relative to that in the vein, the wall structure of the substantially weaker vein becomes dilated, so that its cross-section grows to reach a multiple of its original cross-section until the vein wall becomes adapted to the higher pressure and the considerably increased blood flow per unit of time. The vein which has been "arterialised" in this manner may then, over many years in favourable cases, be punctured directly before each treatment with one large lumen cannula (about 1.6 to 2 mm inner diameter) for the blood outflow and with another for the blood return. The cannulas are removed after treatment. The punctures heal up naturally. This method of vessel access has the drawback that the optimum anatomical and biological transformation and formation of the so-called "Cimino-Brescia-Fistel" requires a time period of several weeks to some months. Moreover, the anatomical and functional transformation is not always good, and each scar formed after a puncture leads to a weakening of the blood vessel wall. It is therefore basically more satisfactory if the connection between the patient and the artificial kidney is made by a single catheter only.

It has already been proposed to connect an additional device having a valve function to a single cannula. This arrangement operates by the blood being drawn through the cannula, then the valve being changed over, and the blood being then returned through the same cannula. This so-called "single-needle" method requires considerable additional equipment and increased cost.

However, a double lumen catheter for connecting the artificial kidney to the patient having separate ducts for the inflowing and outflowing blood streams and thus requiring only one puncture is known. In this double lumen catheter, the inner duct of the inner cannula is provided for the inflowing blood stream and an annular duct between the inner cannula and an outer cannula surrounding the inner cannula is provided for the outflowing blood stream. In this double lumen catheter, the inner cannula is ground to a sharp edge to facilitate puncture of the blood vessel. The front end of the outer cannula, which does not project as far as the front end of the inner cannula, tapers conically towards the outer wall of the inner cannula, and comprises draw-off openings directly behind this conical region in the form of three bores. The drawback of this type of catheter is that this form of transition between the outer diameter of the inner cannula and the outer diameter of the outer cannula is costly to construct, and the particular form of draw-off opening leads to a high draw-off resistance, a turbulent flow and dead corners where the blood is static in the most forward part of the annular duct between the inner and outer cannulae. This means that this known cannula tends to suffer from the formation of coagula and blockage of the annular duct. Furthermore, these are difficulties in inserting the double lumen catheter into the blood vessel lumen because of the fact that the surface of the outer cannula is interrupted by the bores.

A double lumen catheter is also known in which the outer cannula is ground to a sharp edge to facilitate puncture of a blood vessel. The inner cannula is drawn back before a puncture is made until its front end is completely behind the sharp ground end of the outer cannula. When the outer cannula is lying securely in the blood vessel after puncture, the inner cannula is slid forward until its front end projects beyond the front end of the outer cannula. This double lumen catheter has the drawback of immediately forming a large puncture equal in diameter to the outer diameter of the outer cannula. A further disadvantage is that because of the fact that the two cannulas are slideably disposed relative to one another over a fairly large distance, this known double lumen catheter construction is costly to manufacture and relatively complicated to handle.

In a further known double lumen catheter, the inner cannula is removably disposed in a connection piece connected to the rear end of the outer cannula. To make the puncture, the inner cannula is replaced by a puncture portion which has an outer diameter equal to the inner diameter of the outer cannula, and projects beyond the front end of the outer cannula when it is slid in. This projecting end of the puncture portion gradually tapers to a diameter similar to the outer diameter of the inner cannula which is to be inserted subsequently, and is sharply ground at its front end to facilitate puncture. After puncture of a blood vessel, the puncture portion is pulled out and replaced by the inner cannula, which has connections at a substantially Y-shaped connection portion for the inner duct of the inner cannula and the annular duct formed between the outside of the inner cannula and the inside of the outer cannula. The inner cannula is slid into the outer cannula until its front end projects beyond the front end of the outer cannula. The connection piece for the outer cannula also comprises a valve which automatically closes on pulling out the puncture portion and automatically opens on sliding in the inner cannula through the inner cannula connection piece. This double lumen catheter is expensive to manufacture and complicated to handle.

An object of the invention and its embodiments is to mitigate the drawbacks of known double lumen catheters by providing a double lumen catheter of the above-described type, which is of a more simple construction and is therefore less costly to manufacture, and is considerably easier to use.

The present invention provides a double lumen catheter for use in haemodialysis, which comprises ducts for blood streams flowing into and respectively out of the body, an inner cannula providing an inner duct, an outer cannula surrounding the inner cannula and providing between the inner cannula and the outer cannula an outer duct, a front end of at least the inner cannula being inclined obliquely to the longitudinal cannula axis and sharply ground to facilitate puncture of a blood vessel, the front end of the inner cannula projecting beyond a front end of the outer cannula and the cross-section of the catheter changing progressively from the outer diameter of the inner cannula to the outer diameter of the outer cannula, the outer duct when in an operative state having at its front end an opening of cross-sectional area equal to the cross-sectional area of the outer duct, so that the total cross-section of the outer duct is available to a blood stream entering or leaving the outer duct.

An advantage of the double lumen catheter according to the invention is that the puncture is made by the inner cannula, which is of smaller outer diameter than the outer cannula. A relatively small opening is therefore cut, which as the double lumen catheter is further inserted into the blood vessel becomes stretched or widened relatively slowly to finally become equal to the outer diameter of the outer cannula. The artificial kidney can then be immediately connected. The double lumen catheter according to the invention is thus easier to handle and manufacture than known double lumen catheters. As the outer duct in its operating state comprises at its front end an opening extending over the entire cross-section of the outer duct, the opening does not have a high draw-off resistance, neither does it give rise to static regions or the danger of turbulent flow.

According to a preferred feature of the invention, to obtain a gradual transition between the outer diameter of the inner cannula and the outer diameter of the outer cannula, the outer cannula may be cut obliquely to its longitudinal axis and rest against the inner wall of the outer cannula at the most forward region of its front end.

In a further preferred embodiment of the invention, the outer cannula is also ground to a sharp edge. In this manner, the resistance to puncture afforded by the blood vessel may be reduced, but at the cost of a larger puncture opening.

A further possibility of reducing the resistance to puncture is to provide the inner cannula with a larger outer diameter at its front end where it projects beyond the outer cannula than in the region in which the inner cannula is surrounded by the outer cannula. In a desirable development of this preferred feature of the invention, the inner cannula comprises, in that region in which it projects beyond the front end of the outer cannula, a firmly fitted jacket cut obliquely in the longitudinal direction of the cannula and sharply ground to facilitate puncture.

In a further embodiment of the invention, a conical portion is mounted on the outside of the inner cannula, its smallest outer diameter being equal to the outer diameter of the inner cannula and its largest outer diameter being of the same dimensional order as the outer diameter of the outer cannula.

The conical portion may comprise a contact surface for the front end of the outer cannula, with the inner cannula and outer cannula being slidable relative to each other in the longitudinal direction. When using this embodiment, after making the puncture the outer cannula is drawn back relative to the inner cannula until the outer clearance duct comprises at its front end an opening which extends over the total clearance duct cross-section.

In a desirable development of this embodiment of the invention, a conically tapering region extends from the contact surface of the conical portion, its smallest outer diameter being equal to the outer diameter of the inner cannula and its largest outer diameter being equal to the inner diameter of the outer cannula. This conically tapering region aids guiding and centering.

Finally, an atoxic substance of bactericidal effectiveness may be applied to the outer circumferential surface of the outer cannula. The advantage of this is that it has an anti-bacterial effect on the puncture.

The invention is described hereinafter in greater detail by way of example only and with reference to embodiments shown in the accompanying drawings, in which:

FIG. 3 is a further modification of the double lumen catheter of FIG. 1;

FIGS. 4a and 4b show a further embodiment of the invention, wherein the inner cannula and outer cannula are slidable relative to each other in the longitudinal direction, FIG. 4a showing the outer cannula in its forward position and FIG. 4b showing it in its withdrawn position.

Figure 1:
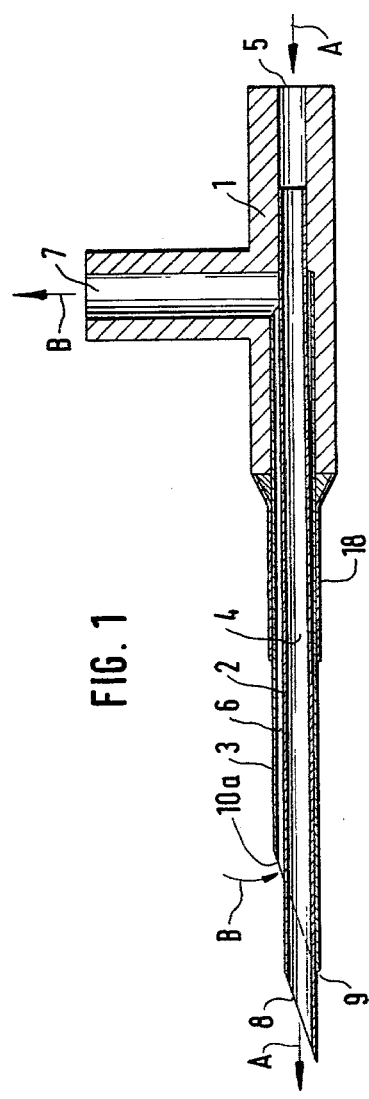
FIG. 1 is a diagrammatic longitudinal section through a double lumen catheter according to the invention.
Figure 2:
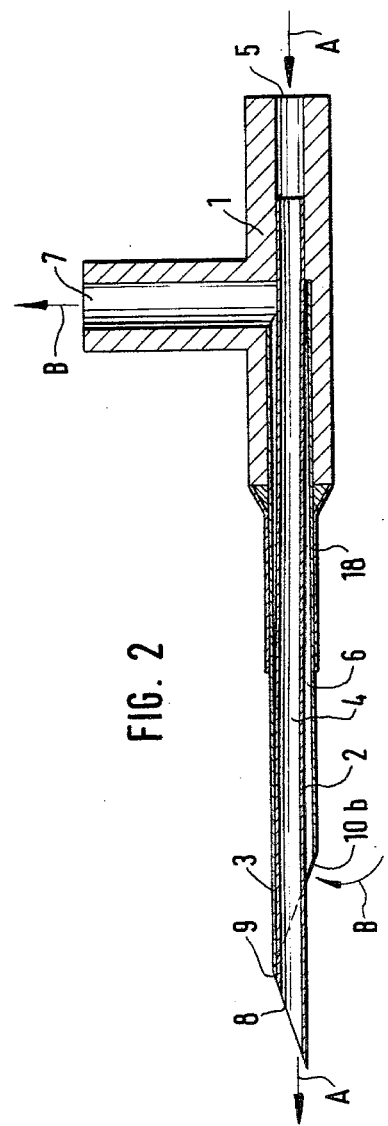
FIG. 2 is a modified embodiment of the double lumen catheter of FIG. 1.

The double lumen catheter shown in FIGS. 1 to 3 each comprise an inner cannula 2 and an outer cannula 3 in a substantially T-shaped connection piece 1. An inner duct 4 of the inner cannula is provided for the blood stream flowing into the body in the direction of the arrow A. The blood stream is fed to the inner duct 4 through a connection tube (not shown) which is fitted into an inlet opening 5. An outer clearance duct 6 is provided for the blood stream flowing from the body of the patient in the direction of the arrow B, being of annular form between the outer wall of the inner cannula 2 and the inner wall of the outer cannula 3, and opening into a transverse duct 7 in the T piece 1. From the end of the transverse duct 7, the blood stream flows in the direction of the arrow B through a connection tube (not shown) to an artificial kidney.

The arrangement is such that the inner cannula 2 projects beyond a front end of the outer cannula 3. The front end 8 of the inner cannula 2 is cut obliquely to the cannula axis, and is sharply ground to facilitate puncture of a blood vessel. The transition between the outer diameter of the inner cannula 2 and the outer diameter of the outer cannula 3 is gradual. There are several ways of achieving this. In the embodiment shown in FIGS. 1 and 2, the arrangement is such that the inner cannula 2 lies at its most forward end region 9 against the inner wall of the outer cannula 3. The front end 10 or 10b of the outer cannula 3 is cut obliquely to the longitudinal direction of the cannula. The two embodiments shown in FIGS. 1 and 2 differ only by the different relation between the obliquely cut front end of the outer cannula and the obliquely cut front end 8 of the inner cannula. The operation of the double lumen catheter shown in FIGS. 1 and 2 is such that the puncture opening is firstly cut by the sharply ground front end 8 of the inner cannula 2, and is then gradually widened by further insertion of the double lumen catheter into this opening until it equals the outer diameter of the outer cannula 3. An opening extending over the total cross-section of the clearance duct is available at its front end for the entry into the clearance duct 6 of the blood stream flowing from the body in the direction of the arrow B.

In the embodiment shown in FIG. 3, the inner cannula 2 has a larger outer diameter at its front end 11, where it projects beyond the outer cannula, than in the region in which the inner cannula 2 is surrounded by the outer cannula 3. For this, a firmly fitted jacket 12 is provided in the region 11, its front end 12a being cut obliquely to the longitudinal direction of the cannula and sharply ground to facilitate puncture. A gap 14 is provided between the rear end 12b of the jacket 12 and the front end 10a of the outer cannula 3 to make it possible for the blood stream flowing from the body in the direction B to enter the outer duct 6.

A modified embodiment of the double lumen catheter according to the invention is shown in FIGS. 4a and 4b. A substantial difference between this embodiment and the embodiments shown in FIGS. 1 to 3 is that the outer cannula 3 in the T piece 14 is slidable relative to the inner cannula 2. Sliding can take place between contact surface 19 and contact surface 15, this latter being provided on a frusto-conical portion 16 fixed on to the outside of the inner cannula 2. The frusto-conical portion 16 gradually varies in outer diameter from the outer diameter of the inner cannula 2 to the outer diameter of the outer cannula 3, so as to provide a gradual transition between the outer diameter of the inner cannula and the outer diameter of the outer cannula to facilitate puncture. From frusto-conical portion 16 a conically tapering region 17 extends rearwardly from the contact surface 15, its smallest outer diameter being equal to the outer diameter of the inner cannula and its largest outer diameter being equal to the inner diameter of the outer cannula. The region 17 facilitates guiding and centering.

The puncture is made with the inner cannula 2 positioned relative to outer cannula 3 as shown in FIG. 4a. The initially relatively small puncture opening equal to the outer diameter of the inner cannula 2 is widened by the action of the frusto-conical part 16 until it equals the outer diameter of the outer cannula 3. When the outer cannula 3 of the double lumen catheter lies in the blood vessel, the inner cannula 2 and outer cannula 3 are slid relative to each other to attain the position shown in FIG. 4b. This has the effect of making the outer duct 6 freely accessible at its front end 6a for the inflowing blood.

A layer 18 of an atoxic substance of bactericidal effect, such as silver, may be applied to the outer circumference of the outer cannula 3 in all the embodiments.

We claim:

1. A double lumen catheter for use in haemodialysis, which comprises ducts for blood streams flowing into and respectively out of the body, an inner cannula providing an inner duct, an outer cannula surrounding the inner cannula and providing between the inner cannula and the outer cannula an outer duct, said outer cannula including a smooth and continuous outer surface defined by an imperforate wall, a front end of at least the inner cannula being inclined obliquely to the longitudinal cannula axis and sharply ground to facilitate puncture of a blood vessel, the front end of the inner cannula projecting beyond a front end of the outer cannula and defining an axially open passage of said inner duct, the cross-section of the catheter changing progressively from the outer diameter of the inner cannula to the outer diameter of the outer cannula, the outer duct when in an operative state having at its front end an axially open passage of cross-sectional area equal to the cross-sectional area of the outer duct, so that the total cross-section of the outer duct is available to a blood stream entering or leaving the outer duct.

2. A double lumen catheter as claimed in claim 1, wherein so as to obtain the progressive change of cross-section the front end of the outer cannula is also inclined obliquely to its longitudinal axis and contacts an inner wall of the outer cannula at the most forward region of the front end of the outer cannula.

3. A double lumen catheter as claimed in claim 2, wherein the front end of the outer cannula is sharply ground.

4. A double lumen catheter as claimed in claim 1, having an atoxic bactericidal substance on an outer surface of the outer cannula.

5. A double lumen catheter for use in haemodialysis, which comprises ducts for blood streams flowing into and respectively out of the body, an inner cannula providing an inner duct, an outer cannula surrounding the inner cannula and providing between the inner cannula and the outer cannula an outer duct, said outer cannula including a smooth and continuous outer surface a front end of at least the inner cannula being inclined obliquely to the longitudinal cannula axis and sharply ground to facilitate puncture of a blood vessel, the front end of the inner cannula projecting beyond a front end of the outer cannula, said projecting front end portion having a larger outer diameter than the portion of the inner cannula surrounded by the outer cannula, and the cross section of the catheter changing progressively from the outer diameter of the inner cannula to the outer diameter of the cannula, the outer duct when in an operative state having at its front end an opening of cross-sectional area equal to the cross-sectional area of the outer duct, so that the total cross-section of the outer duct is available to a blood stream entering or leaving the outer duct.

6. A double lumen catheter as claimed in claim 5, wherein to the front end portion of the inner cannula which projects beyond the front end of the outer cannula is attached a jacket inclined obliquely at its front end to the longitudinal direction of the inner cannula and sharply ground to facilitate puncture of a blood vessel.

7. A double lumen catheter as claimed in claim 5, wherein the projecting front end portion of the inner cannula includes a frusto-conical portion mounted on the outside of the inner cannula, said frusto-conical portion having a smallest outer diameter equal to the outer diameter of the inner cannula, and a largest outer diameter substantially equal to the outer diameter of the outer cannula.

8. A double lumen catheter as claimed in claim 7, wherein the frusto-conical portion has a contact surface for the front end of the outer cannula, the inner cannula and outer cannula being slidable relative to each other in the longitudinal direction.

9. A double lumen catheter as claimed in claim 8, wherein a further conically tapering portion extends rearwardly from the contact surface of the frusto-conical portion, its smallest outer diameter being equal to the outer diameter of the inner cannula and its largest outer diameter being equal to the inner diameter of the outer cannula.

* * * * *